United States Patent [19]

Gowhari

[11] Patent Number: 5,636,787
[45] Date of Patent: Jun. 10, 1997

[54] EYEGLASSES-ATTACHED AROMATIC DISPENSING DEVICE

[76] Inventor: Jacob F. Gowhari, 5403 Newcastle Ave., #24, Encino, Calif. 91316

[21] Appl. No.: 450,777

[22] Filed: May 26, 1995

[51] Int. Cl.⁶ ................................................. A61L 9/00
[52] U.S. Cl. ................................................. 239/36; 239/56
[58] Field of Search ................ 239/36, 289; 351/51, 351/52

[56] References Cited

U.S. PATENT DOCUMENTS

| | | | |
|---|---|---|---|
| 2,109,092 | 2/1938 | Roll | 239/36 |
| 2,560,681 | 7/1951 | Berkowitz | 239/36 X |
| 4,580,581 | 4/1986 | Reece et al. | 239/289 X |
| 4,620,778 | 11/1986 | Bertolli | 351/51 |
| 4,874,129 | 10/1989 | DiSapio et al. | 239/36 |
| 4,968,128 | 11/1990 | Mendola | 239/36 |

*Primary Examiner*—Kevin Weldon
*Attorney, Agent, or Firm*—Albert O. Cota

[57] ABSTRACT

An eyeglasses-attached aromatic dispensing device (10) that consists of a pair of eyeglasses (12) that are separated by a bridge section and that have a temple attached to the outer edge of each eyeglass. The device (10) features an aromatic module (30) that can be designed to be attached to either the temple (16) or to the bridge section (14). The module (30) includes an absorbent cavity (40) that has inserted an absorbent material (50) to which is added a selectable perfume or cologne. The module (30) has an outer wall (44) that has at least one opening (46) through which the aroma of the perfume or cologne is dispensed into the surrounding environment.

8 Claims, 3 Drawing Sheets

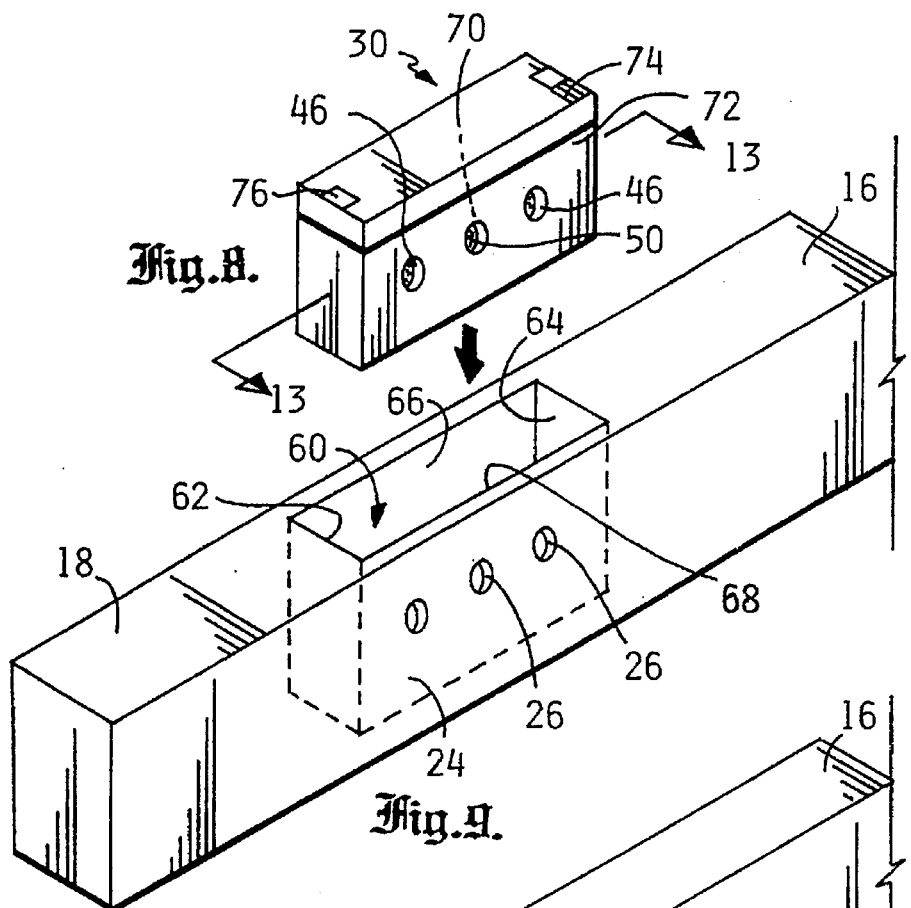
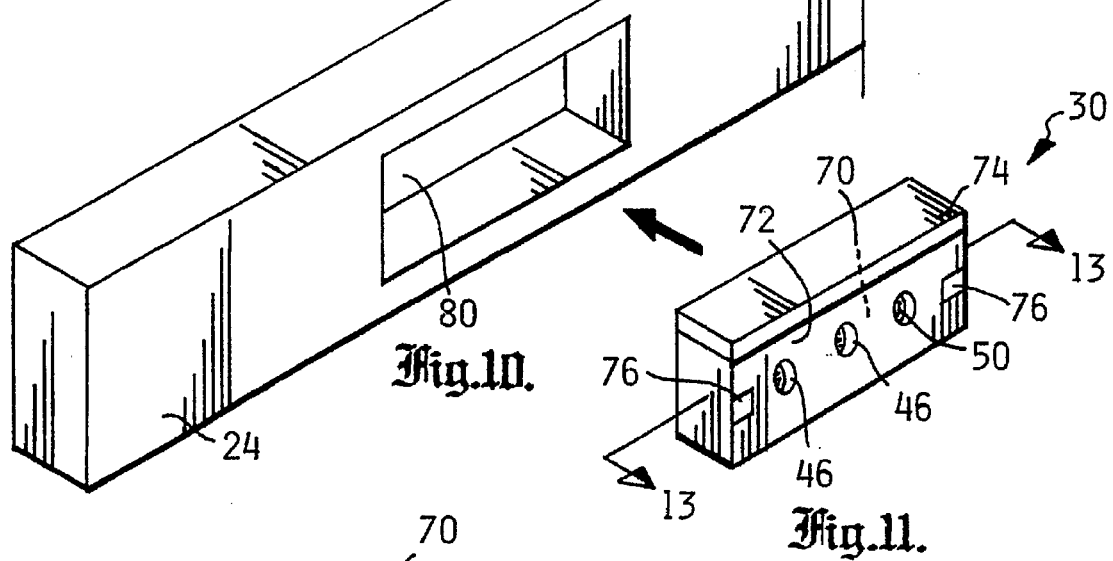
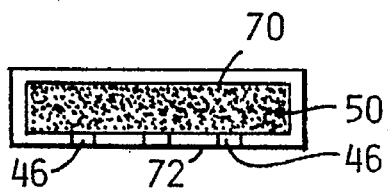

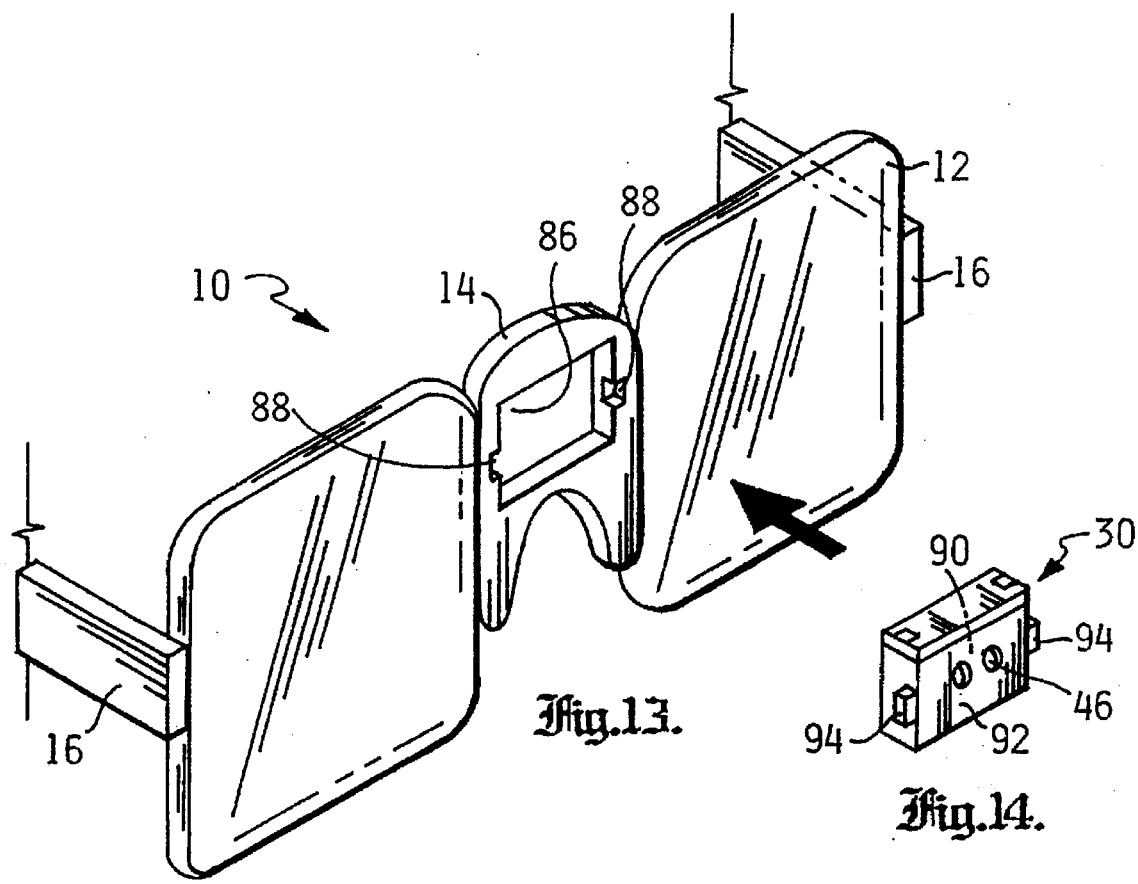
Fig.13.
Fig.14.
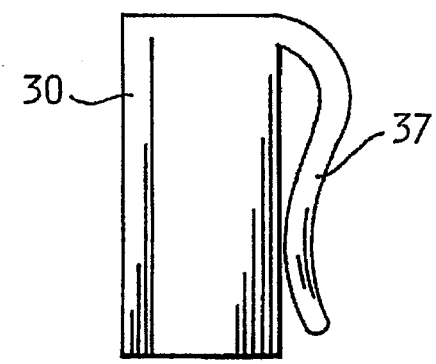
Fig.15.

EYEGLASSES-ATTACHED AROMATIC DISPENSING DEVICE

TECHNICAL FIELD

The invention pertains to the general field of perfume and cologne dispensers and more particularly to an aromatic dispenser that is attached to a pair of eyeglasses.

BACKGROUND ART

The use of perfume and colognes, especially by females, has been popular throughout recorded history. Perfumes because of their high cost and potency, are typically stored in small glass bottles. To use a perfume, a small quantity is applied to the tip of a finger which is than rubbed or dabbed on selected areas of the human body. Colognes are generally lass expensive and can be more liberally applied and dispensed by several means.

Colognes are generally stored in some type of a dispenser. These dispensers which are available in many designs, sizes and shapes, typically consist of atomizer assemblies, air wicks emersed in a container filled with a cologne, or aromatic dispensers that are designed to be loosely placed on a flat surface or attached by an adhesive to a wall. The aromatic dispensers include a structure that contains an absorbent containing the cologne and an outward surface. The outward surface has fixed openings or a rotatable section that when rotated, the absorbent is exposed which then allows the scant of the cologne to ba dispensed into the surrounding environment.

A search of the prior art which included U.S. patents, catalogs and other literature did not disclose any perfume or cologne dispensers having a dispensing structure that is designed to be attached to a pair of eyeglasses. However, the following U.S. patents were considered related:

| U.S. Pat. No. | INVENTOR | ISSUED |
| --- | --- | --- |
| 4,806,008 | Tarloff | 21 February 1989 |
| 4,798,455 | Yoe, et al | 17 January 1989 |
| 3,179,950 | Gross, et al | 20 April 1965 |
| 2,243,769 | Nerney | 27 May 1941 |

The U.S. Pat. No. 4,806,008 to Tarloff discloses an eyeglass temple having an oblong shaped recess in its inner side. Retained within the recess is a removable identification strip that is protected by a removable transparent flexible material.

The U.S. Pat. No. 4,798,455 to Yoe, discloses a user reconfigurable novelty glasses that include separate eyeglass frames and temples. The frames and temples may be readily combined with each other and with other separate eyeglass frames and temple pieces to form a variety of novelty sunglasses. The invention features a design that allows each eyeglass frame to be used with either the user's right or left eye and each temple piece may be used over either the user's right or left temple and ear.

The U.S. Pat. No. 3,179,950 to Gross, discloses an ornamental frame member located above the lens rim. The frame member is specifically designed to be easily attached and detached from the lens rim.

The U.S. Pat. No. 2,243,769 to Nerney discloses an eyeglass construction that includes a bridge section to which are pivotally attached at each side, a temple. The bridge includes a slot therethrough into which is inserted a block insert.

For background purposes and as indicative of the art to which the invention is related, reference may be made to the following U.S. patents found in the search.

| | INVENTOR | ISSUED |
| --- | --- | --- |
| 4,620,778 | Bertolli | 4 November 1986 |
| 3,667,834 | Davison et al | 6 June 1972 |
| 3,133,141 | Anderson | 12 May 1964 |
| 3,021,753 | Vinson | 20 February 1962 |
| 2,842,028 | Belgard | 8 July 1958 |
| 2,835,063 | Worthington | 20 May 1958 |

DISCLOSURE OF THE INVENTION

The eyeglasses-attached aromatic dispensing device in its most basic form consists of two elements: a pair of eyeglasses and an aromatic module. The eyeglasses include a bridge section that separates the individual eyeglasses and a temple that is attached to the outer edge of each eyeglass. The aromatic module has a means for being attached to the eyeglasses; fop adding and storing a quantity of perfume or cologne; and for allowing the aroma from the perfume or cologne to be dispensed from the aromatic module.

The aromatic module is disclosed in three designs. In the first design, the module includes a temple slot that allows the module to be inserted over a temple at selectable positions along the length of the temple. The second design allows the module to be inserted into a temple cavity that may be located on the side or the top of a temple. In the third design, the module is designed to be removably inserted into a module opening located on the bridge section of the eyeglasses.

In all three designs, the aromatic module incorporates an absorbent cavity into which is inserted and packed an absorbent material which can consist of a felt material, a sponge material or a cotton mixture material. Into the absorbent material is then added a quantity of perfume or cologne. The scent of the perfume or cologne is than dispensed through one or more openings located on an outer wall of the module into the surrounding environment. The module also includes a removable cap that allows additional perfume or cologne to be added to the absorbent material when the aromatic scent has been depleted.

In view of the above disclosure, it is the primary object of the invention to provide an aromatic module that dispenses an aromatic scent and that can be easily attached to a temple or to the bridge section of a pair of eyeglasses.

In addition to the primary object of the invention, it is also an object of the invention to provide a device that:

can be manufactured in various colors to match or accent the color of the eyeglasses, can be selectively located along the longitudinal length of the temple, can be designed to accommodate various designs of temples and bridge sections and, is cost effective from both a manufacturers and consumer points of view.

These and other objects and advantages of the present invention will become apparent from the subsequent detailed description of the preferred embodiment and the appended claims taken in conjunction with the accompanying drawings.

BRIEF DESCRIPTION OF THE DRAWINGS

FIG. 8 is a perspective view of a second design of an aromatic module.

FIG. 9 is a partial perspective view of a temple having a downward extending module cavity dimensioned to receive the aromatic module of FIG. 8.

FIG. 10 is a partial perspective view of a temple having a module cavity located on its side.

FIG. 11 is a perspective view of an aromatic module that is dimensioned to be inserted into the module cavity of FIG. 10.

FIG. 12 is an upper sectional view of an aromatic module having inserted into its absorbent cavity an absorbent material.

FIG. 13 is a partial perspective view of a pair of eyeglasses having an eyeglass bridge section that includes a module opening.

FIG. 14 is a perspective view of a third design of an aromatic module dimensioned to be inserted into the module cavity of FIG. 13.

FIG. 15 is a side elevational view of the first design of the aromatic module that has an inner wall comprised of a resilient clip.

BEST MODE FOR CARRYING OUT THE INVENTION

The best mode for carrying out the invention is presented in terms of a preferred embodiment that, as shown in FIGS. 1–15, is comprised of two major elements: a pair of eyeglasses 12 and an aromatic module 30. The aromatic module is designed to be attached to the eyeglasses, from where it dispenses an aromatic scent.

Figure 1:
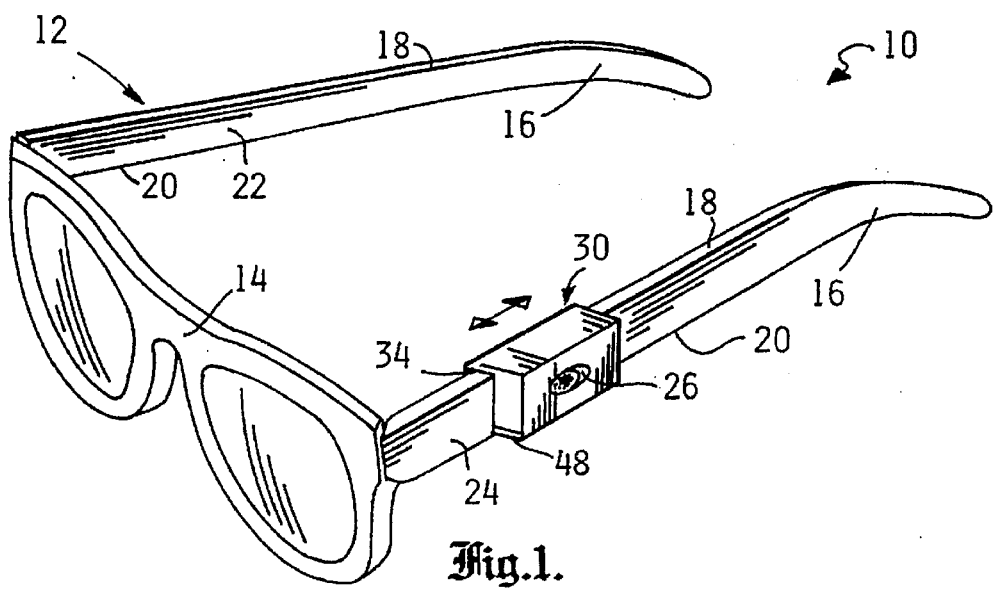
FIG. 1 is a perspective view of a pair of eyeglasses having a first design of an aromatic module attached to one of the temples.
Figure 2:
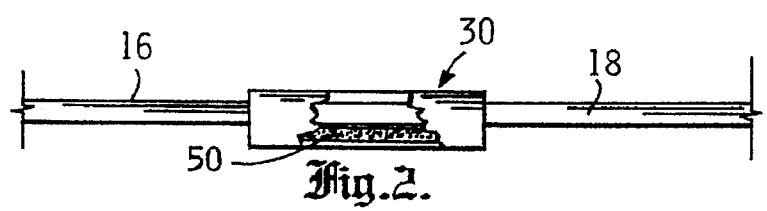
FIG. 2 is a top plan view and cross sectional view of an aromatic module attached to a temple.
Figure 3:
FIG. 3 is a side elevational view and cross sectional view of an aromatic module attached to a temple.
Figure 4:
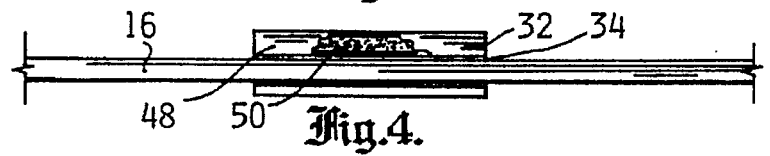
FIG. 4 is a bottom plan view and cross sectional view of an aromatic module attached to a temple.

The eyeglasses 12 are typically shown in FIG. 1 and include a bridge section 14 that separates the two eyeglasses and a pair of temples 16 that extend outward from the outer end of each eyeglass. Each temple has an upper surface 18, a lower surface 20, an inner surface 22 and an outer surface 24.

The primary inventive element of the eyeglasses-attached aromatic dispensing device 10 is the aromatic module 30 which is disclosed in three designs.

The first and preferred design of the aromatic module 30 is shown in FIGS. 1–6. This first design includes a lower surface 32 where from one side extends upward a temple slot 34. The slot 34 has an inner wall 36, an outer wall 38 and is dimensioned to be inserted over the upper surface 18 of at least one of the temples 16 as shown in FIG. 1. As also shown in FIG. 1 by a double arrow the aromatic module 30 can be inserted over a selected distance along the longitudinal length of the temple 16.

Figure 5:
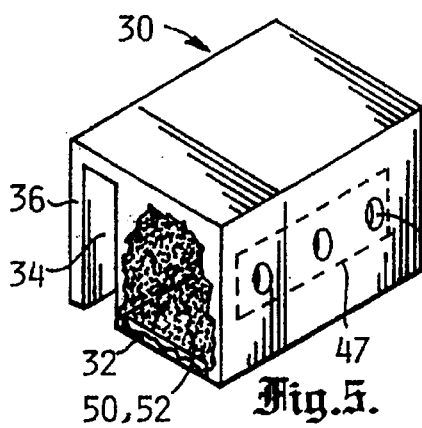
FIG. 5 is a perspective view and cross sectional view of a first design of an aromatic modulo.
Figure 6:
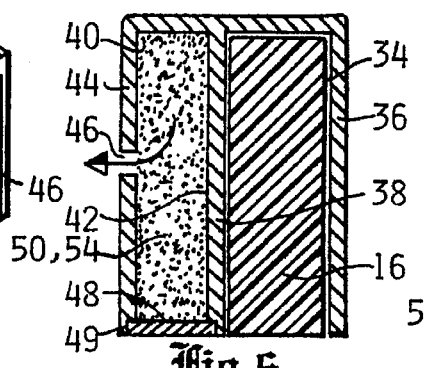
FIG. 6 is a sectional end view of a first design of an aromatic module.
Figure 7:
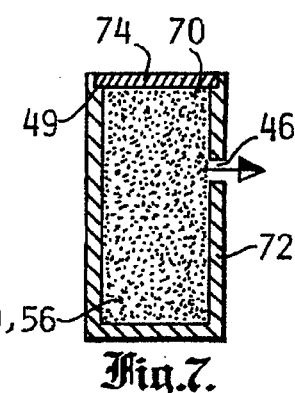
FIG. 7 is a sectional end view of a second of an aromatic module.

The aromatic module 30 as shown in FIGS. 5 and 6, also includes an absorbent cavity 40 that is located adjacent the temple slot 34 as best shown in FIG. 6. The cavity 40 has an inner wall 42, which is also the outer wall 38 of the temple slot 34, and an outer wall 44. The outer wall has therethrough at least one opening 46 as shown in FIG. 1 or preferably three openings 46 as shown in FIG. 5. Into the absorbent cavity is inserted and packed an absorbent material 50 which can consist of either a felt material 52 as shown in FIG. 5, a sponge material 54 as shown in FIG. 6, or a cotton mixture material 58 as shown in FIG. 7. To the absorbent material 50 is then added a quantity of perfume or cologne. After the addition of the perfume or cologne, a removable lower cap 48 is attached by a removable attachment means 49 to seal the absorbent cavity 40 as best shown in FIG. 6. Alternatively, in lieu of removing the cap 48, the perfume or cologne may be added to the absorbent material by an eye dropper inserted into the the openings 46. Also, during the time the aromatic module 30 is being stored or otherwise not being used, a tape 47 as shown by the broken lines in FIG. 5, may be placed over the openings 46 of the module 30 to prevent the dissipation of the perfume or cologne.

The second design of the eyeglasses-attached aromatic dispensing device 10 is shown in FIGS. 7, 8 and 9 In this design, the temple 16 as shown in FIG. 9 is made with a module cavity 60 that extends downward from the upper surface 18 of the temple 16. The cavity 60 includes a front surface 62, a rear surface 64, an inner surface 66 add an outer surface 68. The outer surface 68 of the module cavity 60 includes therethrough at least one opening 26 and preferably three openings as shown in FIG. 9.

The aromatic module 30 used with the second design has a downward extending cavity 70 with an outer wall 72 that also has therethrough at least one but preferably three openings 46 as shown in FIG. 8. When the aromatic module 30 is inserted into the module cavity 60 in the temple, the opening(s) 46 on the module 30 are in alignment with the opening(s) 26 in the temple 16. As with the first design, an absorbent material 50 is inserted into the downward extending cavity 70 and thereafter, to the absorbent material is added a quantity of perfume or cologne. After the addition of the perfume or cologne, an upper cap 74 is attached to the open upper end of the cavity 70. The cap includes a removable attachment means and on at least one end, a gripping slot 76 that allows the attached cap to be easily removed when it is time to add more perfume or cologne to the absorbent material.

The third design which is shown in FIGS. 10 and 11, is similar to the second design with the difference being that the temple 16 includes a module cavity 80 that extends inward from the outer surface 24 of the temple 16 as shown in FIG. 10. The aromatic module 30 used with the third design as shown in FIG. 11, is identical to the aromatic module 30 used with the second design. In FIG. 12 is shown a cross sectional view taken along the lines 13–13 of FIGS. 8 and 11.

The fourth design of the eyeglasses-attached aromatic device 10 as shown in FIGS. 13 and 14, utilizes the bridge section 14 of a pair of eyeglasses in lieu of the temples 16. In this design, the bridge section 14 has a substantially centered module opening 86 as shown in FIG. 13. The opening includes a gripping slot 88 located at each side of the opening.

The aromatic module 30 of the fourth design as shown in FIG. 14 has a downward extending cavity 90 that has an outer wall 92 that has therethrough at least one opening 46. Extending outward from each side of the module is an outward extending tab 94. When the module 30 is inserted into the module opening 86 with the outer wall 92 facing outward and with the outward extending tabs 94 interfacing with the respective gripping slots 88, the module 30 is held in place within the module opening 86.

As shown in FIG. 15, the first design of the aromatic module 30 can be molded with an inner wall 36 that is comprised of a resilient clip 37. The clip allows the module 30 to be clipped to the temple 16 or some other similar structure.

While the invention has been described in complete detail and pictorially shown in the accompanying drawings it is not to be limited to such details, since many changes and modifications may be made in the invention without department from the spirit and scope thereof. For example, the aromatic module 30 of the first design can be designed with an upper section that is curved and constructed of various light weight materials such as aluminum or a plastic preferred. Also, the aromatic module can be designed so that the absorbent material 50 can be easily removed and replaced when a different fragrance of perfume or cologne is desired. Hence it is described to cover any and all modifications and forms which may come within the language and scope of the appended claims.

I claim:

1. An eyeglasses-attached aromatic dispensing device comprising:
    a) a pair of eyeglasses separated by a bridge section and having attached to the outer edges of each eyeglass, a temple having an upper surface, a lower surface, an inner surface, and an outer surface,
    b) an aromatic module having:
        (1) a lower surface from where one side extends upward, a temple slot that is dimensioned to be inserted over the upper surface of at least one of said temples,
        (2) means for storing a quantity of perfume or cologne, and
        (3) means for allowing the aroma from the perfume or cologne to be dispensed from said aromatic module into the surrounding environment.

2. The device as specified in claim 1, wherein said means for storing a quantity of perfume or cologne into said aromatic module comprises:
    a) said aromatic module having an absorbent cavity located adjacent said temple slot, wherein said cavity to filled with an absorbent material to which is added a quantity of perfume or cologne and,
    b) a removable lower cap that seals said absorbent cavity after the addition of the perfume or cologne.

3. The device as specified in claim 2 wherein said absorbent material comprises a felt material.

4. The device as specified in claim 2 wherein said absorbent material comprises a sponge material.

5. The device as specified in claim 2 wherein said absorbent material comprises a cotton mixture material.

6. An eyeglasses-attached aromatic dispensing device comprising:
    a) a pair of eyeglasses separated by a bridge section and having attached to the outer edges of each eyeglass, a temple having an upper surface, a lower surface, an inner surface, and an outer surface,
    b) an aromatic module having;
        (1) means for being attached to at least one of the temples,
        (2) means for storing a quantity of perfume or cologne, and
        (3) an outer wall further having at least one opening through which the aroma of said perfume or cologne is dispensed into the surrounding environment.

7. An eyeglasses-attached aromatic dispensing device comprising:
    a) a pair of eyeglasses separated by a bridge section and having attached to the outer edges of each eyeglass, a temple having an upper surface, a lower surface, an inner surface, and an outer surface,
    b) an aromatic module comprising:
        (1) a lower surface where form one side extends upward a temple slot that is dimensioned to be inserted over the upper surface of at least one of said temples,
        (2) an absorbent cavity located adjacent said temple slot and having at least one opening,
        (3) an absorbent material that is inserted and packed into said absorbent cavity to which is added a quantity of perfume or cologne, and
        (4) a removable lower cap that seals said absorbent cavity and that when removed allows a quantity of perfume or cologne to be added to said absorbent material.

8. The device as specified in claim 1 wherein said temple slot further comprises a resilient clip that allows said aromatic module to be clipped over the upper surface of said temple.

* * * * *